United States Patent
Dautova et al.

(10) Patent No.: US 10,598,556 B2
(45) Date of Patent: Mar. 24, 2020

(54) METHOD FOR IN-SITU MARKERS FOR THERMAL MECHANICAL STRUCTURAL HEALTH MONITORING

(71) Applicant: United Technologies Corporation, Hartford, CT (US)

(72) Inventors: Lyutsia Dautova, Rocky Hill, CT (US); Wendell V. Twelves, Jr., Glastonbury, CT (US); Joe Ott, Enfield, CT (US); Evan Butcher, Manchester, CT (US); Gary A. Schirtzinger, Glastonbury, CT (US); Rainer J. Herbert, Ellington, CT (US)

(73) Assignee: United Technologies Corporation, Farmington, CT (US)

( * ) Notice: Subject to any disclaimer, the term of this patent is extended or adjusted under 35 U.S.C. 154(b) by 841 days.

(21) Appl. No.: 15/112,127

(22) PCT Filed: Aug. 8, 2014

(86) PCT No.: PCT/US2014/050296
§ 371 (c)(1),
(2) Date: Jul. 15, 2016

(87) PCT Pub. No.: WO2015/026540
PCT Pub. Date: Feb. 26, 2015

(65) Prior Publication Data
US 2017/0067788 A1 Mar. 9, 2017

Related U.S. Application Data

(60) Provisional application No. 61/868,297, filed on Aug. 21, 2013.

(51) Int. Cl.
*B22F 5/04* (2006.01)
*B33Y 40/00* (2015.01)
(Continued)

(52) U.S. Cl.
CPC .............. *G01L 1/25* (2013.01); *B22F 3/1055* (2013.01); *B22F 5/04* (2013.01); *B23K 26/342* (2015.10);
(Continued)

(58) Field of Classification Search
None
See application file for complete search history.

(56) References Cited

U.S. PATENT DOCUMENTS

| | | |
|---|---|---|
| 5,480,439 A | 1/1996 | Bisek et al. |
| 5,490,426 A | 2/1996 | Shiga et al. |

(Continued)

FOREIGN PATENT DOCUMENTS

| | | |
|---|---|---|
| CN | 1588019 A | 3/2005 |
| CN | 102608144 A | 7/2012 |

(Continued)

OTHER PUBLICATIONS

First Chinese Office Action, for Chinese Patent Application No. 201480034919.0, dated Jan. 17, 2018, 16 pages.

(Continued)

*Primary Examiner* — Colleen P Dunn
*Assistant Examiner* — Rajinder Bajwa
(74) *Attorney, Agent, or Firm* — Kinney & Lange, P.A.

(57) ABSTRACT

A method of monitoring the residual stress in surface and near surface regions of a component includes identifying predetermined locations on the surface of a component that are expected to experience high stress during normal operating conditions of the component. Marker particles are introduced into the component during additive manufacture of the component at the predetermined locations. Then, the residual stress of the component is measured at a location corresponding with the marker material using x-ray techniques.

9 Claims, 3 Drawing Sheets

(51) Int. Cl.
| | |
|---|---|
| *B33Y 10/00* | (2015.01) |
| *B23K 26/342* | (2014.01) |
| *G01L 1/25* | (2006.01) |
| *G01N 23/20* | (2018.01) |
| *B22F 3/105* | (2006.01) |
| *F01D 21/00* | (2006.01) |
| *B23K 26/70* | (2014.01) |
| *B23K 103/14* | (2006.01) |

(52) U.S. Cl.
CPC ............ *B23K 26/702* (2015.10); *B33Y 10/00* (2014.12); *B33Y 40/00* (2014.12); *F01D 21/003* (2013.01); *G01N 23/20* (2013.01); *B22F 2003/1056* (2013.01); *B23K 2103/14* (2018.08); *Y02P 10/295* (2015.11)

(56) References Cited

U.S. PATENT DOCUMENTS

| | | | |
|---|---|---|---|
| 5,817,945 A | 10/1998 | Morris et al. | |
| 5,942,444 A | 8/1999 | Rittenburg et al. | |
| 6,254,703 B1 | 7/2001 | Sokol et al. | |
| 7,286,893 B1 * | 10/2007 | Mazumder | B23K 26/34 700/145 |
| 7,918,141 B1 * | 4/2011 | Sathish | F01D 5/286 73/105 |
| 8,923,480 B2 | 12/2014 | Wang et al. | |
| 2001/0045416 A1 | 11/2001 | Sokol et al. | |
| 2002/0051514 A1 | 5/2002 | Ruud | |
| 2008/0095311 A1 | 4/2008 | Zheng et al. | |
| 2009/0117589 A1 | 5/2009 | Southern | |
| 2011/0103933 A1 * | 5/2011 | Olesen | G01B 11/16 415/118 |
| 2015/0362898 A1 * | 12/2015 | Potter | G05B 19/4099 700/98 |

FOREIGN PATENT DOCUMENTS

| | | |
|---|---|---|
| CN | 102998312 A | 3/2013 |
| CN | 103056364 A | 4/2013 |
| CN | 103076115 A | 5/2013 |
| JP | S59150332 A | 8/1984 |
| JP | 2002296125 A | 10/2002 |
| JP | 2005-241308 A | 9/2005 |
| JP | 2008506127 A | 2/2008 |
| JP | 2013040876 A | 2/2013 |
| JP | 2013104673 A | 5/2013 |
| WO | 2012174232 A2 | 12/2012 |

OTHER PUBLICATIONS

Dutta, B., et al., "Additive Manufacturing by Direct Metal Deposition", Advanced Materials & Processes, May 2011, pp. 33-36.

Fitzpatrick, et al., "Measurement Good Practice Guide No. 52, Determination of Residual Stresses by X-ray Diffraction—Issue 2", Open University, National Physical Laboratory, QinetiQ, Manchester Materials Science Centre, Stresstech Oy, ISSN 1744-3911, Sep. 2005, www.npl.co.uk.

International Search Report and Written Opinion dated Nov. 21, 2014, for corresponding PCT Application No. PCT/US2014/050296.

Jian Chen, "Hybrid Design Based on Wire and Arc Additive Manufacturing in the Aircraft Industry", Thesis, Cranfield Univ., Dec. 2012.

Japanese Office Action, for Japanese Patent Application No. 2016-536290, dated Feb. 27, 2018, 10 pages.

Extended European Search Report, for European Patent Application No. 14838637.8, dated Mar. 6, 2017, 6 pages.

International Preliminary Report on Patentability for PCT Application No. PCT/US2014/050296, dated Feb. 23, 2016, Pages 7.

* cited by examiner

METHOD FOR IN-SITU MARKERS FOR THERMAL MECHANICAL STRUCTURAL HEALTH MONITORING

BACKGROUND

This invention relates generally to the field of additive manufacturing. In particular, the invention relates to an additive manufacturing process enabling the measurement of residual stresses at specific locations in components.

Additive manufacturing is a process by which parts can be made in a layer-by-layer fashion by machines that create each layer according to an exact three dimensional (3D) computer model of the part. In powder bed additive manufacturing, a layer of powder is spread on a platform and selective areas are joined by sintering or melting by a directed energy beam. The platform is indexed down, another layer of powder is applied, and selected areas are again joined. The process is repeated for up to thousands of times until a finished 3D part is produced. In direct deposit additive manufacturing technology, small amounts of molten or semi-solid material are applied to a platform according to a 3D model of a part by extrusion, injection or wire feed and energized by an energy beam to bond the material to form a part. Common additive manufacturing processes include selective laser sintering, direct laser melting direct metal deposition, and electron beam melting.

Once the component is manufactured, the component is incorporated into a system to be used for a specific function. An example is a gas turbine engine. During operation, the component is exposed to thermal and mechanical environments that stress the component. The stresses and resulting strain experienced by the component cause residual stresses and possible structural failures or cracks in the component.

Several non-destructive techniques exist to detect crack growth or residual stresses in components. Current non-destructive techniques expose the component to external probes such as electromagnetic fields, dyes, or ultrasonic waves. It is difficult to obtain localized information at pre-determined locations in a component with the current technologies, for example at regions of increased service stresses. Current technologies mostly detect flaws after they have formed, and are far less sensitive to the stage leading up to the formation of flaws, for example, internal cracks.

SUMMARY

A method of monitoring the residual stress of a component of a base alloy formed by additive manufacturing includes identifying pre-determined locations on the component that experience high stress during normal operating conditions of the component. Marker particles are introduced into surface and near surface regions of the component during additive manufacture of the component at the pre-determined locations. The residual stress of the component is measured at the marker particle locations.

A component formed by additive manufacturing and further subjected to stress during operation contains marker materials inserted in the surface and near surface regions of the component at various predetermined locations over the surface of the component. The markers allow residual stress measurements to be made on the component at the site of each marker material.

DETAILED DESCRIPTION

Figure 1:
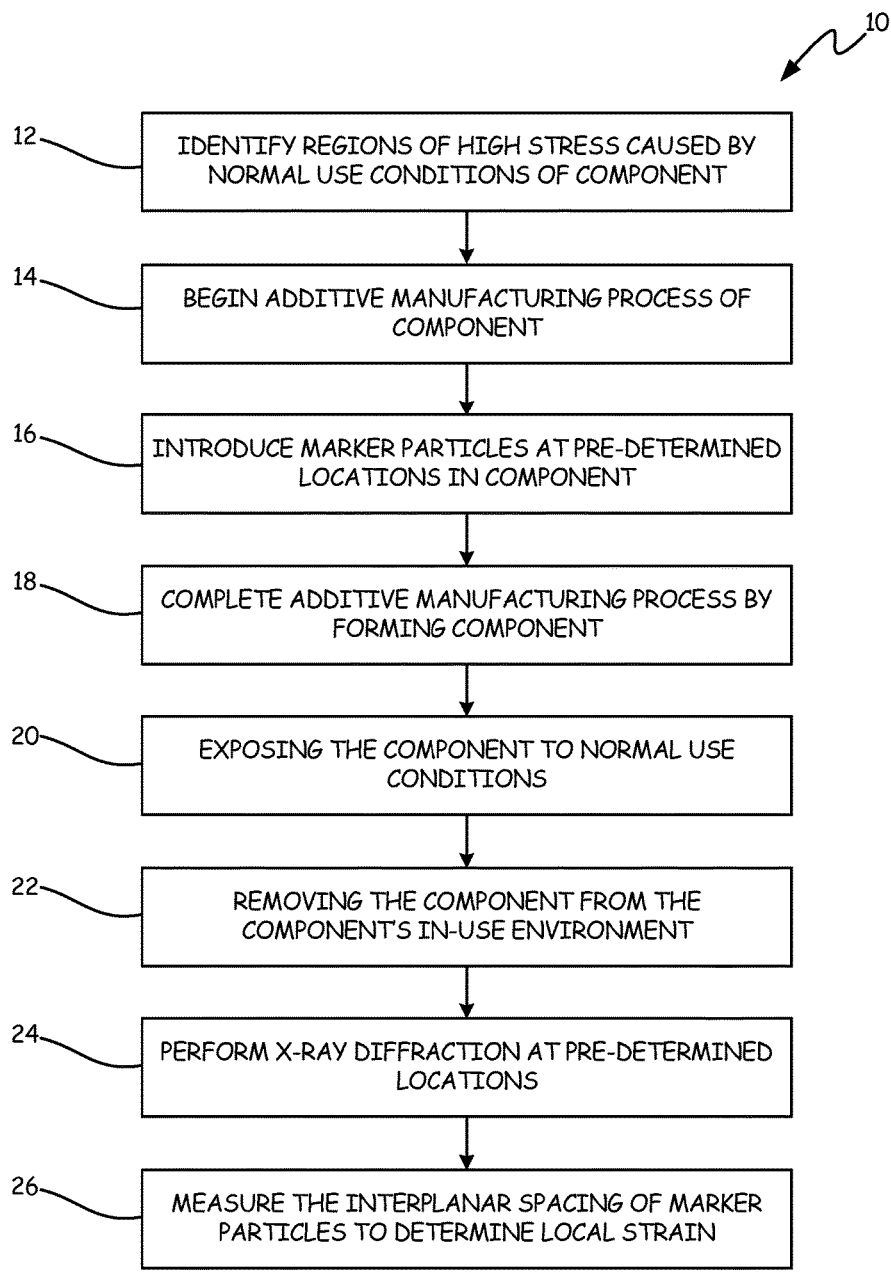
FIG. 1 is a flow diagram representing the method of monitoring residual stress in a component.

FIG. 1 is a flow diagram representing the method of monitoring residual stress. Method 10 involves, first, the identification of high stress regions caused by normal use conditions of a component (Step 12). In the next step, an additive manufacturing process is initiated (Step 14). Marker particles are introduced at pre-determined high stress locations of the component during manufacture (Step 16). The additive manufacturing process is then completed (Step 18), and the component is put into service under normal use conditions (Step 20). The component is removed from service when necessary (Step 22). X-ray diffraction measurements are made in the regions where the marker particles are located (Step 24) to determine interplanar spacing of the marker particles in order to determine local internal elastic strain and internal residual stress. (Step 26).

X-ray diffraction techniques to measure residual stress in a metal component are well-known in the art and rely on the fact that an internal elastic stress will change the interplanar spacing of a crystalline solid under stress from the interplanar spacing of the same material in a stress-free state. The interplanar spacing is determined from the well-known Bragg's law $$n\lambda = 2d \sin \theta$$

where $\lambda$ is the incident x-ray wavelength, d is the interplanar spacing, $\theta$ is the diffraction angle of a diffraction peak and n is an integer. If $d_1$ is the interplanar spacing of a stressed metal in a certain crystallographic direction and $d_0$ is the spacing of the same metal in the same direction in a stress free state, the residual strain in that direction $\varepsilon$ is:

$$\varepsilon = . \frac{d_1 - d_0}{d_0}$$

Residual stress in an elastically isotropic material can be determined from the strain by multiplying the strain with an appropriate term containing the elastic modulus and Poisson's ratio. An example reference discussing x-ray measurements of residual stress is "Determination of Residual Stresses by X-ray Diffraction—issue 2" by Fitzpatrick et al., National Physical Laboratory of the UK (available at www.npl/co/uk), which is incorporated herein in its entirety.

The marker particles inserted into the additive manufactured component are chosen as to not interact with the component material by alloying, by the formation of second phases or by other forms of solution or interaction. The interplanar spacing change of the markers can then be used as a measure of internal stress of a component containing the markers in the vicinity of the markers. The interplanar spacings of the marker material in the as-built condition are taken to be the stress free reference values.

The marker particles are inserted into the surface and near surface regions of the component for the measurement of residual stress by x-rays. The penetration of x-rays into a metal component is typically on the order of a few microns.

An example marker material for use with titanium alloy turbine components such as Ti-6A1-4V is cerium. Cerium is nearly insoluble in titanium, there are no intermetallic compounds in the Ti—Ce binary system, and cerium, due to its large atomic mass, produces a relatively strong x-ray signal. Dysprosium and samarium are other candidates.

Figure 2:
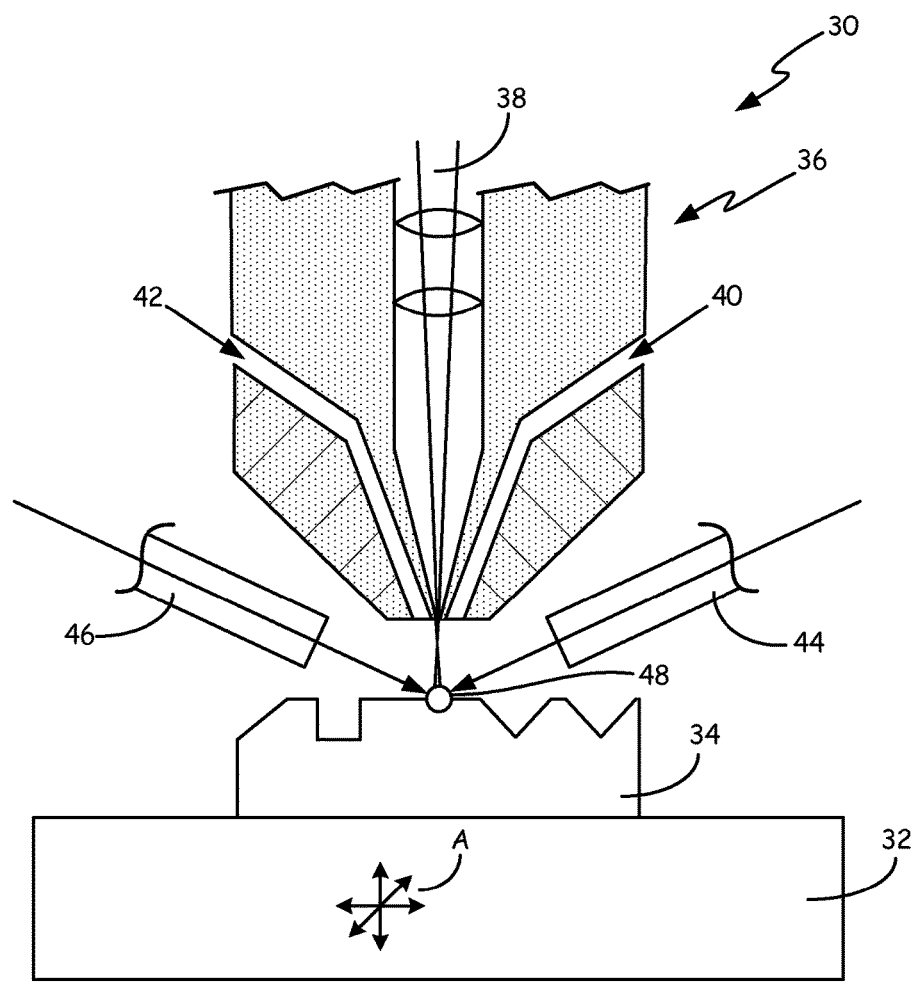
FIG. 2 is a schematic diagram of a direct metal deposition process.

An additive manufacturing process suitable for use with the present method is direct metal deposition (DMD). A schematic of a direct metal deposition process is shown in FIG. 2. DMD process 30 includes base 32, workpiece 34, deposition unit 36 and sensors 46 and 48. Base 32 is capable of three axis computer controlled positioning as schematically indicated by arrows A. Deposition unit 36 contains channels 40 and 42 that may carry deposition powders and inert gas to the deposition site. Deposition unit 36 further contains a laser energy source (not shown) and associated optics 38. Deposition unit 36 is capable of five axis computer controlled positioning during a build. Output from sensors 44 and 46 is used to control the build of workpiece 34. Workpiece 34 is formed by laser 38 melting small region 48 on workpiece 34 into which powders are introduced through channels 42 and 44. The build is a point-by-point process according to a CAD model of workpiece 34 model stored in memory of the control system of device 30.

In the present invention, when marker regions are required, marker particles replace the normal build particles being deposited in melt pool 48. The size of the marker regions may be from 0.1 microns to over a millimeter depending on the requirements.

Figure 3:
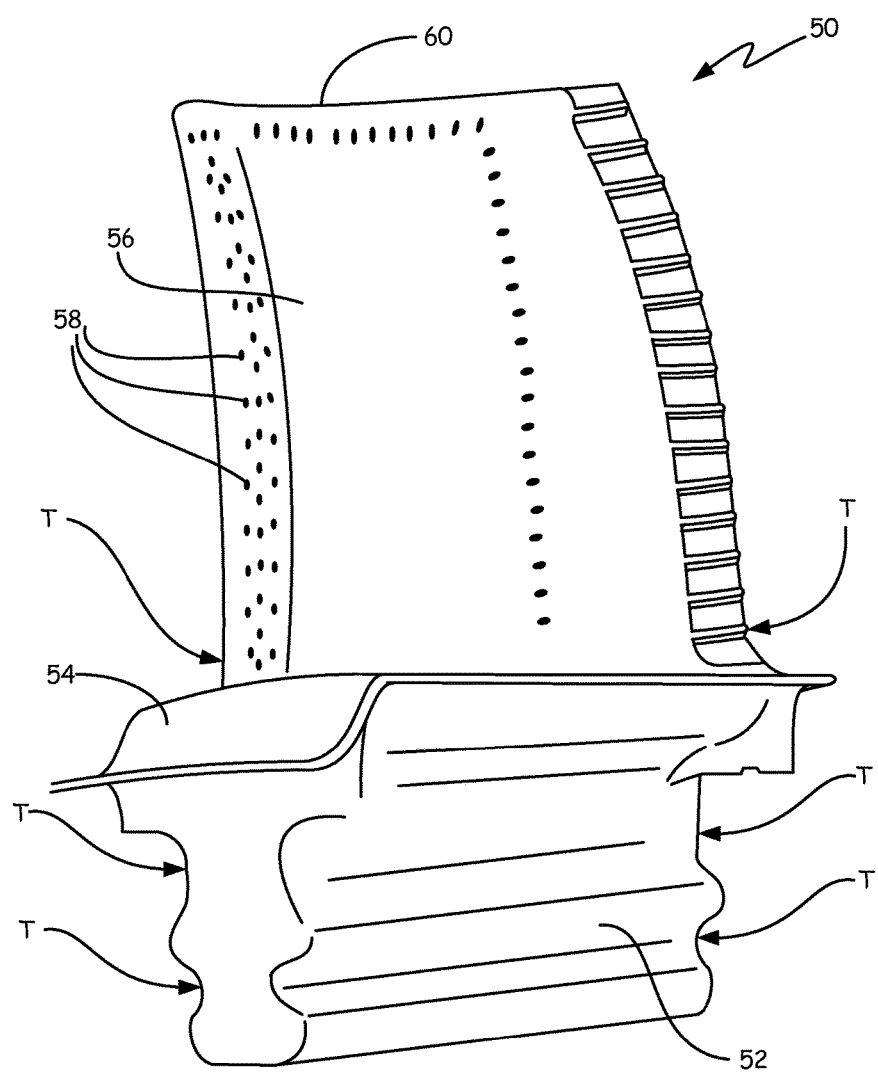
FIG. 3 is a perspective view of a turbine blade.

A perspective view of exemplary turbine blade 50 is shown in FIG. 3. Turbine blade 50 comprises root 52, platform 54, airfoil 56 with cooling passages 58 and tip 60. High stress regions on blade 50 during service are predominantly in transition regions such as between airfoil 56 and platform 54 and in curved regions in root 52 all indicated by arrows T. It is these regions where markers of the present invention are placed during an additive manufacturing build such as that shown in FIG. 2 to monitor the residual stress generated during service. The marker materials, to be useful, should exhibit at least the following characteristics. They should not alloy with the base alloy during the additive manufacturing process. They should not form intermetallic phases with the base alloy. They should preferably have a high atomic number for strong X-ray signature. In addition, the diffraction peaks of the marker materials preferably should not overlap the diffraction peaks of the base alloy.

Discussion of Possible Embodiments

The following are non-exclusive descriptions of possible embodiments of the present invention.

A method of monitoring residual stress of a component of a base alloy formed by additive manufacturing may include: identifying a high stress location of a component that experiences high stress during normal operating conditions of the component; introducing during additive manufacturing marker particles in surface and near surface regions to create a marker associated with the identified high stress location of the component; and measuring a residual stress of the component at the marker.

The method of the preceding paragraph can optionally include, additionally and/or alternatively any, one or more of the following features, configurations and/or additional components:

Measuring the residual stress at the marker with x-ray diffraction;

The x-ray diffraction may be used to measure an interplanar spacing of the marker in at least one of the surface and near surface predetermined locations;

A local strain in the marker may be determined from the measured interplanar spacing;

The x-ray diffraction measurement may be performed with an x-ray diffractometer;

The x-ray diffraction may be performed with x-ray beams of about 1 mm to 2 mm in diameter focused on a surface of the component;

The additive manufacturing may include direct metal deposition, direct laser melting or direct laser deposition;

The marker may be insoluble in the base alloy;

The base alloy may include a titanium alloy and the marker may be cerium.

A component of a base alloy formed by additive manufacturing that is subjected to stress during operation may include a marker of a marker material different from the base alloy inserted in surface and near surface regions of the component at a predetermined location to allow residual stress measurements to be made on the component at the marker.

The component of the preceding paragraph can optionally include additionally and/or alternatively any, one or more of the following features, configurations and/or additional components:

The predetermined location may be a region expected to undergo stress during normal operating conditions of the component;

The residual stress measurements may be x-ray diffraction measurements;

The x-ray diffraction measurements may be used to determine residual strain in the marker material by measuring lattice interplanar spacing of the marker material;

The x-ray diffraction measurements may be performed with an x-ray diffractometer;

The x-ray diffraction measurements may use beam sizes of about 1 mm to 2 mm;

The additive manufacturing may include direct metal deposition, direct laser melting or direct laser deposition;

The marker material may be insoluble in the base alloy and may not form a second phase with the base alloy and otherwise may not react with the base alloy;

The base alloy may be a titanium alloy and the marker material may be cerium.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A method of monitoring residual stress of a component of a base alloy formed by additive manufacturing, the method comprising:
    identifying a location of the component that experiences stress during operating conditions of the component;
    introducing during additive manufacturing marker particles in surface and near surface regions to create a marker associated with the identified high stress location of the component; and
    measuring a residual stress of the component at the marker.

2. The method of claim 1, further comprising measuring the residual stress at the marker with x-ray diffraction.

3. The method of claim 2, wherein the x-ray diffraction is used to measure an interplanar spacing of the marker in at least one of the surface and near surface pre-determined locations.

4. The method of claim 3, wherein a local strain at the marker is determined from the measured interplanar spacing.

5. The method of claim 3, wherein the x-ray diffraction measurement is performed with an x-ray diffractometer.

6. The method of claim 3, further comprising performing the x-ray diffraction with x-ray beams of about 1 mm to 2 mm in diameter focused on a surface of the component.

7. The method of claim 1, wherein the additive manufacturing comprises direct metal deposition, direct laser melting or direct laser deposition.

8. The method of claim 1, wherein the marker is insoluble in the base alloy.

9. The method of claim 1 wherein the base alloy comprises a titanium alloy and the marker comprises cerium.

* * * * *